US00RE33801E

United States Patent [19]

Green

[11] E Patent Number: Re. 33,801

[45] Reissued Date of Patent: Jan. 21, 1992

[54] MIXING AND DISCHARGE CAPSULE

[75] Inventor: Russell D. Green, Millsboro, Del.

[73] Assignee: Dentsply Research & Development Corp., Milford, Del.

[21] Appl. No.: 233,866

[22] Filed: Aug. 15, 1988

Related U.S. Patent Documents

Reissue of:

[64] Patent No.: 4,648,532
Issued: Mar. 10, 1987
Appl. No.: 861,481
Filed: May 9, 1986

[51] Int. Cl.[5] ..... B67B 7/48

[52] U.S. Cl. ..... 222/82; 215/DIG. 8; 222/83; 222/136; 222/327; 222/386; 604/87; 604/200

[58] Field of Search ..... 222/80–83, 222/129, 136, 145, 327, 386; 206/219, 222, 63.5; 215/DIG. 8; 604/56, 82, 87–90, 92, 191, 200, 201, 223, 414, 416

[56] References Cited

U.S. PATENT DOCUMENTS

| | | | |
|---|---|---|---|
| 2,404,316 | 7/1946 | Sack | 206/222 |
| 3,144,966 | 8/1964 | Cook | 222/327 X |
| 3,415,360 | 12/1968 | Baumann et al. | 206/222 |
| 3,425,598 | 2/1969 | Kobernick | 222/83 |
| 3,521,745 | 7/1970 | Schwartzman | 206/222 |
| 3,537,605 | 11/1970 | Solowey | 222/386 X |
| 3,595,439 | 7/1971 | Newby | 222/80 |
| 3,655,035 | 4/1972 | Mühlbauer | 206/219 |
| 3,655,037 | 4/1972 | Lussier | 206/222 |
| 3,684,136 | 8/1972 | Baumann | 222/386 |
| 3,739,947 | 6/1973 | Baumann et al. | 222/136 |
| 3,802,604 | 4/1974 | Morane et al. | 222/83 |
| 3,819,091 | 6/1974 | Hollender | 222/327 |
| 3,907,106 | 9/1975 | Purrmann et al. | 222/80 X |

*Primary Examiner*—Kevin P. Shaver
*Attorney, Agent, or Firm*—David E. Wheeler; Dante James Picciano; Dale R. Lovercheck

[57] ABSTRACT

A combination mixing and discharge capsule for storing separate ingredients which are to be mixed together prior to use and including a container body for one ingredient closed at one end by a slidable piston and the opposite end being displaceably received in a cup-shaped cap which forms a second compartment with a perforated wall of the container body opposite the end containing the piston for receiving a frangible pillow containing a liquid second ingredient to be mixed with the ingredient in the body. The cap has a discharge nozzle extending axially therefrom and when the cap is displaced farther onto the body the innermost wall of the pillow is burst to cause the discharge of the liquid ingredient through the perforated wall end into the container body for mixing with the ingredient therein. After mixing is completed, a puncturing rod is inserted into the nozzle to puncture the opposite wall of the pillow and, when the rod is withdrawn the piston is moved toward the perforated wall to effect discharge of the mixed ingredients through the nozzle.

6 Claims, 1 Drawing Sheet

MIXING AND DISCHARGE CAPSULE

Matter enclosed in heavy brackets [ ] appears in the original patent but forms no part of this reissue specification; matter printed in italics indicates the additions made by reissue.

*This is a reissue of application Ser. No. 861,481, filed May 9, 1986, now U.S. Pat. No. 4,648,532.*

BACKGROUND OF THE INVENTION

This invention pertains to a combination mixing and discharge capsule which contains different ingredients in the field of Dentistry but, nevertheless, is also applicable to other fields of use, especially where small quantities of different materials are to be mixed and particularly where a pulverant or granular material is to be mixed with a certain type of liquid material. By way of example, capsules of this type frequently are used in Dentistry to mix certain ingredients to form cements and the like, as well as amalgams and other dental filling mixtures and materials.

It has been relatively common heretofore to provide capsules in which only mixing of different ingredients occurs, without said capsules being provided with any particular means for discharge other than removing a cap from one end of the capsule and removing the enclosed mixture in any convenient manner. One example of such device comprises the subject matter of prior U.S. Pat. No. 3,655,035 dated Apr. 11, 1972 in the name of Muhlbauer. In this patent, pulverant material is contained in a body which is closed at one end by a telescoping cap, and the other end has means to engage a rupturable pillow in which a second ingredient is contained and adaptd to be discharged into the hollow body with the first material and vibrated in a suitable mechanism to effect the mixture, after which the cap is removed to permit the mixture to be removed therefrom but no means to effect discharge by pressure are included in the structure.

A number of other capsules also have been developed which include means for initially containing different ingredients and then mixing the same, followed by discharging the mixture from the body of the capsule through a nozzle or the like. The following prior U.S. Patents represent examples of this type of device:

U.S. Pat. No. 3,537,605—Solowey, Nov. 3, 1970
U.S. Pat. No. 3,595,439—Newby et al, July 27, 1971
U.S. Pat. No. 3,684,136—Baumann, Aug. 15, 1972
U.S. Pat. No. 3,739,947—Baumann, June 19, 1973
U.S. Pat. No. 3,907,106—Purrmann, Sept. 23, 1975

In the foregoing patents, although they are provided with discharge means as well as the mixing of initially separated materials in a common mixing chamber, certain improvements have been developed in the instant invention which are believed to offer advantages over the aforesaid prior art both from the stand point of manufacture and ease of assembly and operation, details of which are set forth below.

SUMMARY OF THE INVENTION

It is among the objects of the present invention to provide a container body which preferably is molded from plastic material, for example, but without restriction thereto, said body being hollow and adapted to contain a first ingredient, such as powdered material and the same is initially contained in the compartment by a plunger telescopically mounted in one initially open end of the container body and the opposite end of the body has a perforated transverse wall integral therewith to form one end of a second compartment in which a rupturable pillow containing a second, usually liquid ingredient, the second compartment being completed by use of a cup-like cap which is displaceable on said body and is also provided with an elongated nozzle co-axial with the cap and container body and the arrangement being such that when the cap is displaced farther onto the body, preferably the wall of the pillow which is closest to the perforation is ruptured and continued pressuring from the cap forces the liquid material into the mixing compartment where it engages the pulverant material therein and, by vibration, mixing occurs and is followed by suitably rupturing the opposite wall of the pillow by inserting a piercing member into the nozzle, after which the plunger is moved towards the nozzle to forcibly eject the mixed material therethrough. If desired, the discharge may be effected directly into a prepared cavity in a tooth, for example, especially if the mixture is a filling material or, if it is a cement, discharge may be effected directly onto the desired area.

Another object of the invention is preferably to provide the container in form of a pillow having opposed walls, jointly sealed at the peripheries thereof, said walls being formed from suitable metal foil sheet material, for example, or plastic material, or a laminate thereof, and the wall which is placed closest to the perforated end of the container body is rendered more readily rupturable than the opposite wall preferably by being thinner than said opposite wall but said opposite wall also being capabe of being perforated by a piercing rod or otherwise when discharge of the material is to be effected.

A further object of the invention is to provide a piston of simple design and jointly serving as a closure for the initially open end of the container body but being provided with no required means to effect removal of the piston from the body inasmuch as the same is only intended and designed for operating as a piston to effect discharge of mixed material from the nozzle which extends from the cap which is threaded onto the opposite end of the container body.

Still another object of the invention is to provide on the container body means by which the body may engage a seat in an appropriate pressure apparatus, either manually or power-operated, and thus suitably position the capsule for operation of the discharge piston for movement within the container body in the direction of the nozzle of the cap thereon.

Details of the foregoing objects and of the invention are set forth in the following specification and illustrated in the accompanying drawings comprising a part thereof.

DETAILED DESCRIPTION OF PREFERRED EMBODIMENTS OF THE INVENTION

Figure 1:
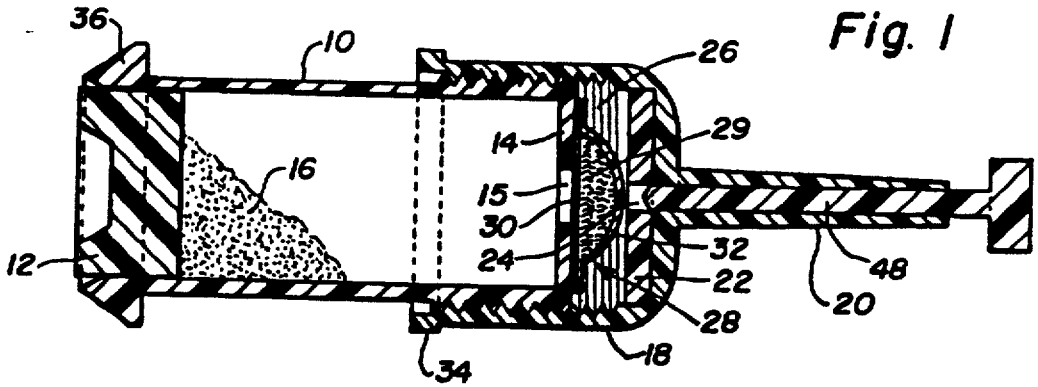
FIG. 1 is a longitudinal sectional view of a capsule embodying principals of the present invention and is illustrated with the parts of the desired initial positions thereof in the capsule.

Referring to FIG. 1, there is illustrated therein a container body 10 which preferably is molded from suitable plastic material but may also be made from other appropriate material such as, for example, metal. One end of the body is open initially and is closed by a combination closure and piston 12 which may be made from any suitable material such as plastic or rubber-like materials suitable to render the same operable effectively as a piston which is telescopically inserted into said initially open end of the body 10.

The opposite end of the body has an integral transverse wall 14 that is provided with a preferably central perforation 15. One exemplary ingredient 16, of measured quantity for example, is filled into the interior of the container body 10 before the piston 12 inserted therein.

Threadably fitted onto the opposite end of the body 10 which as the wall 14 thereon is a cup-like cap 18 and the other end of the cap has an orifice that is an integral discharge nozzle 20 formed therewith. One the interior of the end of the cap from which the nozzle 20 extends, a gasket disc 22 is mounted and is provided with a central hole or perforation 24 which is aligned with the inlet end of the nozzle 20. Within the cap 18 between the wall 14 and disc 22 is a second compartment 26 within which a container, preferably a so-called pillow 28, in positioned. Said pillow is formed preferably from suitable metal foil material which is impervious to a selected liquid material, such as mercury, or otherwise. Another appropriate material would be a suitable plastic sheet material or a laminate of plastic and metal foil. For convenience, suitable discs of the material are formed, and one or both of them are bulged in order to provide a cavity in which a second ingredient 29 is contained and the discs are sealed at the edges of peripheries. In the preferred construction, the opposite discs actually comprise walls and the wall 30 is oriented toward, abuts and is disposed against the wall 14. The wall 30 of the frangible container or pillow 14 is preferably thinner than the opposite wall 32, for purposes to be described below.

When mixing of the materials 16 and [28] *29* is to be effected, the cap 18 is displaced farther onto the container body 10 for purposes of decreasing the space or compartment 26 and thereby cause the gasket 22 to co-act with wall 14 to compress pillow 28 by moving the wall 32 toward wall 30. When pressure is sufficient, wall 30 will rupture adjacent perforation 15 and thereby cause discharge of the material [28] *29* into the compartment which already contains materials 16, somewhat as in the manner illustrated in FIG. 2 and in which the pillow 28 has been substantially completely compressed, but the wall 32 usually has not been penetrated at this time in the operation.

The preferred means to effect displacement of the cap 18 on body 10 are complementary threads respectively thereon but it is to be understood that other displacement means may be used in lieu of threads. To facilitate the rotation and threading of the cap 18 onto the container body 10, the initially open end of the cap 18 may be provided with an annular rim 34 which, if desired, may be serrated to effect desired gripping thereof. Also, the end of the container body 10 in which the piston 12 is mounted also preferably has another annualar rim or flange 36 formed thereon and, if desired, the periphery thereof may also be serrated to facilitate gripping the same for effecting relative rotation between the body 10 and cap 18. The flange 36 also suitably is used to abut a shoulder, for example in a discharging apparatus or tool 38 which, as specifically illustrated in FIG. 4, is of a manual type having ears 40 to receive for example two fingers of a human hand, while a thumb may be applied against the button 42 in order to force the plunger 44 against piston 12, as shown in FIG. 4.

Figure 3:
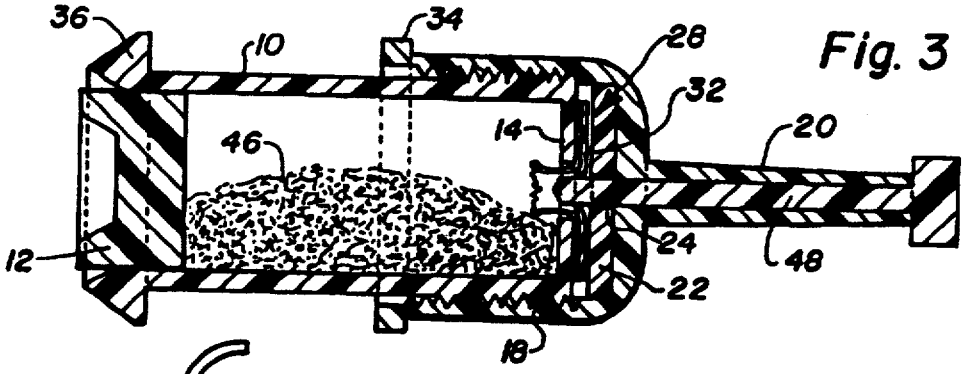
FIG. 3 is another longitudinal sectional view similar to the preceeding figures and especially FIG. 2 but in which the second wall of the pillow has been penetrated by a piercing tool and the figure otherwise showing a mixture of the two materials within the capsule body.
Figure 4:
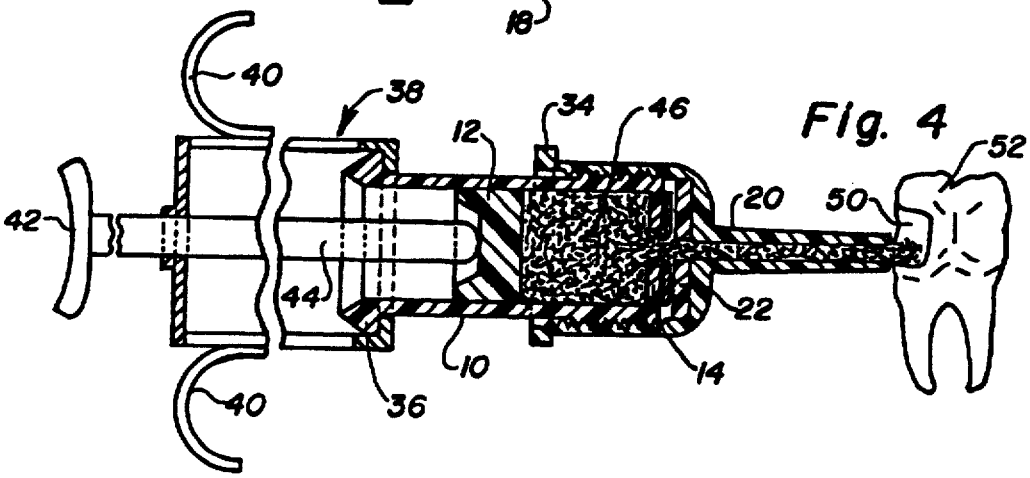
FIG. 4 is an exemplary illustration of the capsule shown in the preceeding figures and especially in FIG. 3 as being mounted within one example of a pressure apparatus, specifically of a manual type, by which the piston is in process of forcibly discharging mixed material from the nozzle into an exemplary prepared cavity in a tooth.

In order to effect discharge of the mixed material 46 from the container body 10, attention is directed to FIG. 3 in which it will be seen that the nozzle 20 has had a piercing rod 48 projected therein, preferably for the full length, for example, in order to extend through the perforation 24 in gasket 22 and thereby pierce the disc or wall 32 of pillow 28, following which piercing rod 48 is removed and thereby clears the interior of nozzle 20 to receive the material 46 as it is forcibly ejected from nozzle 20 by inward movement of the piston 12, either by the exemplary type of apparatus 38 shown in FIG. 4 or some other manual or power-operated device, as desired.

Figure 2:
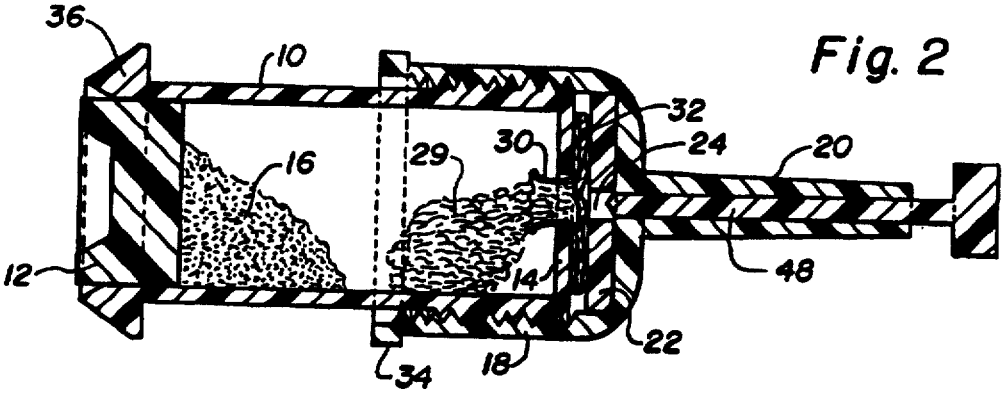
FIG. 2 is another longitudinal sectional view illustrating the rupturing of a pillow which contains a second ingredient to be mixed with the first ingredient in the capsule.

Initially, as shown in FIGS. 1 and 2, and particularly for purposes of convenience, the exemplary piercing rod 48 may be mounted within the nozzle 20 in partially extended position, as shown in said figure and in which the inner end of the piercing rod is only aligned with the central perforation 24 of gasket 22. By so providing the piercing rod in this manner, there is no need for a dentist or other operator to hunt for a piercing tool and all necessary parts of the capsule are assembled in operative position and ready for use such as in the initial positions thereof illustrated in FIG. 1.

When the capsule has been mounted in discharging position, as shown in FIG. 4 in exemplary manner, it will be seen that in the event that material 46 is of a filling type to be applied to a cavity 50 in tooth 52, the discharging material conveniently may be directly applied to the cavity. However, in the event the material is of a cement nature, with equal facility, it may be applied to a suitable area or surface where usage is needed. Other materials also are readily capable of being mixed within the capsule of the invention and discharged therefrom in a manner as described herein above.

The foregoing description illustrates preferred embodiments of the invention. However, concepts employed may, based upon such description, employed in other embodiments without departing from the scope of invention. Accordingly, the following claims are intended to protect the invention broadly, as well as in the specific forms shown herein.

I claim:

1. A combination mixing and discharge capsule comprising in combination, a body adapted to contain a first ingredient and having a piston in one end and the opposite end having a perforated wall on the body, a cap displaceably connected over the end of the body having the perforated wall and forming therewith a separate compartment, said cap having a discharge orifice in the form of a nozzle extending outwardly away from the opposite end of said body, a frangible container enclosing a second ingredient and disposed in said separate compartment with a wall oriented toward said perforated wall, means operable to displace said cap towards said piston and farther onto said body until at least the wall of the container oriented toward said perforated wall is ruptured to permit discharge of the container contents through said perforation into said container body for mixing with the ingredient therein, means operable to puncture the opposite wall of said container comprising a piercing rod [initially only partially inserted into said nozzle] with the inner end out of contact with said container and the inner end of said rod being extendable through said perforation in said opposite wall to effect perforation of said container, and means to move said piston into said body to engage the mixed ingredients and force the same through said discharge nozzle on said cap.

2. The capsule according to claim 1 on which said means to displace said cap farther onto said body comprises complementary threads on said cap and body.

3. The capsule according to claim 1, in which said piston in said one of said container body also forms a closure therefor to prevent loss of the ingredient in the body of the capsule from said one end.

4. The capsule according to claim 1 further characterized by said frangible container comprising a pillow having a pair of opposite rupturable walls and the edges of said walls being sealed together to enclose said second ingredient therein, said second ingredient being liquid.

5. The capsule according to claim 4 in which one wall of said pillow is oriented toward said perforated wall of the body and disposed thereagainst, said one wall of the pillow being weaker and therefore more readily subject to rupture than the opposite wall thereof.

6. The capsule according to claim 4 in which one wall of the pillow is oriented toward said perforated wall and disposed thereagainst, said one wall of the pillow being thinner than the opposite wall of said pillow to tender it more readily subject to rupture.

* * * * *